United States Patent [19]
Piljac et al.

[11] Patent Number: 5,514,661
[45] Date of Patent: May 7, 1996

[54] IMMUNOLOGICAL ACTIVITY OF RHAMNOLIPIDS

[76] Inventors: Goran Piljac; Visnja Piljac, both of 2323 Shasta Dr., Apt 40, Davis, Calif. 95616

[21] Appl. No.: 520,076

[22] Filed: Aug. 28, 1995

Related U.S. Application Data

[60] Division of Ser. No. 277,975, Feb. 20, 1994, Pat. No. 5,466,675, which is a continuation-in-part of Ser. No. 866,691, Apr. 10, 1992, abandoned.

[51] Int. Cl.$^6$ .................................... A61K 31/715
[52] U.S. Cl. .................. 514/25; 514/814; 514/861; 514/863; 514/864; 514/878; 514/883; 514/885; 514/886; 514/887; 514/889; 514/903; 514/908
[58] Field of Search .............................. 514/25, 814, 861, 514/863, 864, 878, 883, 885, 886, 887, 889, 903, 908

[56] References Cited

U.S. PATENT DOCUMENTS

| | | | |
|---|---|---|---|
| 4,628,030 | 12/1986 | Kaeppeli et al. | 435/101 |
| 4,814,272 | 3/1989 | Wagner et al. | 435/100 |
| 4,902,512 | 2/1990 | Ishigami et al. | 424/450 |
| 4,933,281 | 6/1990 | Daniels et al. | 435/101 |

FOREIGN PATENT DOCUMENTS

WO90/11069  10/1990  European Pat. Off. .

*Primary Examiner*—Ronald W. Griffin
*Attorney, Agent, or Firm*—Oblon, Spivak, McClelland, Maier & Neustadt

[57] ABSTRACT

Methods for treating various autoimmune diseases and for providing immunorestoration, by administering, to a subject in need thereof, an effective amount of a composition having, as active ingredient, one or more rhamnolipids of formula (I)

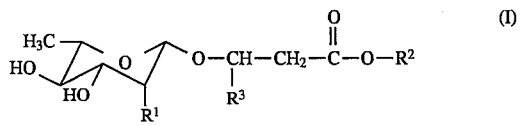

wherein
  $R^1$ is H or α-L-rhamnopyranosyl;
  $R^2$ is H or —CH($R^4$)—CH$_2$—COOH;
  $R^3$ is ($C_5$–$C_{20}$)-saturated, mono or polyunsaturated hydrocarbyl and
  $R^4$ is ($C_5$–$C_{20}$)-saturated, mono or polyunsaturated hydrocarbyl; are provided.

6 Claims, No Drawings

IMMUNOLOGICAL ACTIVITY OF RHAMNOLIPIDS

This application is a Divisional of U.S. patent application Ser. No. 08/277,975, filed Jul. 20, 1994, now U.S. Pat. No. 5,466,675, which is a Continuation-In-Part of U.S. patent application Ser. No. 07/866,691, filed Apr. 10, 1992, abandoned, the text of which is hereby incorporated by reference.

BACKGROUND OF THE INVENTION

1. Field of Invention

The present invention relates to a method for treatment of autoimmune diseases, such as organ specific and organ non-specific autoimmune diseases, AIDS, Parkinson's disease, Alzheimer's disease and amyotrophic lateral sclerosis using rhamnolipids as the active ingredients in the treatment.

2. Description of the Background

Immune response

In immune responses, the ultimate target is an antigen, (bacterium or other invader). Antigen cells, such as macrophages, ingest antigens and fragment them into antigen peptides. Parts of these peptides join to form major histocompatibility complex (MHC) molecules and display themselves on the surface of the cell. T-Lymphocytes have receptors which can recognize a non-native peptides combined with MHC molecules. T-cells are activated and secrete lymphokines, or chemical signals, that mobilize other components of the immune system. Those cells are for the most part B-lymphocytes. B-lymphocytes recognize portions of antigens in various solutions of the body, in which the antigens are not combined with MHC molecules. T-cells cannot recognize the entire antigen. The receptors on T- cells recognize protein fragments of antigens, generally peptides composed of 8 to 15 amino acids.

Consequently, there are two kinds of immune response: (1) Humoral immunity, which occurs through action of B-cells; and (2) cell mediated immunity which occurs through T-cells.

In the case of viral infection, the virus might be able, through mutation, to change its outer envelope rapidly and thus prevent neutralization by antibodies. But when the virus contains proteins within its core that are essential for its life process, that mutation is not permitted. When the virus replicates inside cells, short peptide chains break off from the viral proteins and travel to the cell surface. They serve as ripe targets for the T-cells, which can then attack the infected cell and inhibit the spread of the virus, or as happens in autoimmune diseases, to attack the cells of the body.

T-cells themselves comprise two subpopulations, CD4 (helper) and CD8 (killer) cells. Each type of T-cell uses its own form of MHC to make peptides recognizable. After CD4 cells receive the proper chemical signal, they produce large amounts of lymphokines to accelerate the division of other T-cells. Activated CD8 cells produce much smaller amounts of lymphokines but develop the capacity to punch holes into target cells and to secrete chemicals that kill infected cells or cells which have been in some other way changed.

Autoimmune diseases

Autoimmune diseases occur when T-lymphocytes become activated upon recognizing self antigen linked to the autologous class II molecule of the MHC. One of the key features of autoimmune diseases is that the immune system does not distinguish the body's own components from those of foreign invader's, and thus the body's immune system turns against itself. Genetic factors are obvious contributors as found from studies of identical twins. In the case of multiple sclerosis it has been shown that when one twin gets multiple sclerosis, the other twin has about a 30% chance of acquiring it.

There is also a tendency for more than one autoimmune disorder to occur in the same individual. When this happens, the association is often between diseases within the same region of the autoimmune spectrum. For example, patients with autoimmune thyroiditis have a much higher incidence of pernicious anemia than would be expected from examination of a random population matched for age and sex.

Autoimmune phenomena also tend to aggregate along family lines. It has been shown that the subjects with Hashimoto's disease or pernicious anemia show a high incidence of thyroid and gastric autoantibodies in their first degree relatives. Going from strictly organ specific to less organ specific autoimmune diseases there is a spectrum of autoimmune illnesses as shown below.

Spectrum of Organ Specific Autoimmune Diseases

In descending order, from organ specific to organ non-specific, the list of autoimmune diseases includes: Hashimoto's thyroiditis, Primary myxedema, Thyrotoxicosis, Pernicious anemia, Autoimmune atrophic gastritis, Addison's disease, Premature menopause, Male infertility, Juvenile diabetes, Goodpasture's syndrome, Sympathetic ophthalmia, Phagogenic uveitis, Multiple sclerosis, Psoriasis, Autoimmune hemolytic anemia, Idiopathic thrombocytopenic purpura, Idiopathic leucopenia, Primary biliary cirrhosis, Active chronic hepatitis HBs-ve, Cryptogenic cirrhosis, Pemphygus vulgaris, Ulcerative colitis, Sjogren's syndrome, Poststreptococcal glomerulonephritis, Rheumatoid arthritis, Scleroderma, Wagener's granulomatosis, and Poly/dermatomyositis.

Most of the state of the art approaches to treatment of these diseases involve manipulation of immunological responses. However, in many organ-specific diseases, metabolic control is usually sufficient, such as thyroxine replacement in primary myxedema, insulin in juvenile diabetes, vitamin B12 in pernicious anemia, anti-thyroid drugs for Grave's disease, acetylcholinesterase in myasthenia gravis, thymectomy, steroids in systematic lupus erythematosus and immune complex nephritis, and steroids plus anti-inflammatory drugs like salicylates penicillamine, gold salts in rheumatoid arthritis etc. The efficacy of Cyclosporin A has been proven in such diseases as uveitis, early type I diabetes, nephrotic syndrome and psoriasis, idiopathic thrombocytopenic purpura, systematic lupus erythematosus, polymyositis, Chron's disease, primary biliary cirrhosis, myasthenia gravis, and refractory rheumatoid arthritis.

Some studies suggest that the target for treatment of autoimmune diseases could be the resulting complex of antigen/MHC/T-cell receptor using specific antibodies. Allergic encephalomyelitis is an acute neurological autoimmune disease which is widely regarded as a model for autoimmune disorders and which is mediated by CD4+ T-cells recognizing myelin basic protein (BP), or its peptides, in association with self I-a. Studies have been reported using monoclonal antibodies in treating allergic encephalomyelitis. These monoclonal antibodies bound only the complex of BP and I-as. In vitro, they blocked the proliferative response to the encephalitogenic determinant of BP and reduced the response to intact BP, without affecting the response to a non-relevant antigen-purified protein derivative of tuberculin presented on syngeneic macrophages. They also inhibited experimental allergic encephalomyelitis in H-2s mice. (Aharoni, R; Nature 1991, 351 (6322))

AIDS

The HIV life cycle includes the following steps:

Attachment, Uncoating, Reverse transcription, RNA-ase H degradation, DNA synthesis of second strand, Migration to nucleus, Integration, Latency, Viral transcription, RNA nuclear transport, Protein synthesis, RNA stability, Protein glycosylation, RNA packing and virion assembly, Release of virus, and Maturation.

The most discouraging part of the whole sequence is that HIV has been able to mutate into forms that evade every antiretroviral drug so far tested in man. As a result, many researchers have concluded that in order to beat HIV, they have to bombard HIV with several drugs at once, on the theory that even HIV may not be able to mutate fast enough to become resistant to a multidrug combination. An even better choice would be to have one drug with multiple targets for HIV.

There are three antiretroviral nucleosides currently in human use: 3' azidothymidine, 2'3'-dideoxyinosine and 2'3'-dideoxycytidine. Resistance has been described for each of these nucleosides. Also in clinical use are other reverse transcriptase (RT) inhibitors. Some of them are nucleosides and some are non-nucleosides.

One of the recent and very promising approaches uses protease inhibitors. Protease inhibitors are an attractive target for therapeutic intervention because they act at a postintegration step of HIV replication. Whereas reverse transcriptase inhibitors are only effective in blocking HIV replication when added to culture cells before HIV infection, protease inhibitors are able to inhibit HIV production from chronically infected cells.

An anti-Tat (a regulatory protein required for HIV replication in cultured cells) agent capable of blocking HIV replication in acutely and chronically HIV infected cells could be useful in combination with anti RT agents.

Blocking of viral entry. HIV entry begins with highly specific binding of the HIV gp120 envelope protein with a CD4 molecule on the surface of susceptible cells. In addition, binding of gp120 on the surface of an infected cell with CD4 on the surface of an uninfected cell is involved in syncytia formation and cell-to-cell spread of HIV. A recombinant soluble form of the CD4 receptor (sCD4) or the chimeric CD4-immunoglobulin G (IgG), designed to extend the serum half-life of sCD4, has been shown to effectively block HIV infection and syncytia formation in cultured cells at levels that were attainable clinically. (J. O. Kahn et al, Ann. Intern. Med 112, 254 (1990); D. J. Capon et al. Nature 337, 525 (1989))

Another agent designed to exploit the interaction of CD4 and gp120 is CD4-PE40, a fusion protein between CD4 and two domains of the P. aeruginosa exotoxin A (P. Ashorn et al, Proc. Natl. Acad. Sci. U.S.A. 87, 889 (1992); V. K. Chaudhary et al, Nature 335, 369 (1988)). CD4-PE40 binds to infected cells through interaction with gp120 expressed on the cell surface. One toxin domain facilitates entry of the lethal second domain into the cell, resulting in death of infected cells in culture.

There are many other targets in blocking HIV replication in its different stages of development like nucleic acids and immune reconstitution.

Immune reconstitution approaches to block HIV replication are complemented with manipulation of the immune system. The use of candidate HIV vaccines to increase existing immune responses or stimulate new ones in HIV-infected individuals is reviewed elsewhere (B. F. Haynes, Science 260, 1289 (1993)). Another immunization-based approach is the ex vivo retrovirally mediated introduction of the env gene into analogous fibroblasts (J. F. Warner et al., AIDS Res. Hum. Retroviruses 7, 6445(1991); D. J. Jolly and J. F. Warner, Semin. Immunol. #2, 329 (1990)) which would then be given back to the patient to stimulate anti-env immune responses. Studies of cytotoxic T-lymphocytes (CTLs) generated by immunization of mice with syngeneic cells expressing HIV (IIIB) envelope demonstrated that these CTLs recognize common determinants on diverse HIV strains, including several clinical isolates (S. Chada et al., J. Virol. 67). HIV vaccines can also increase existing immunoresponses (B. F. Haynes, Science 260, 1289; 1993). Certain cytokines, such as tumor necrosis factor(TNF) and interleukin-6 (IL-6) may have some effect on HIV synthesis. Interferon-alfa (IFN-alfa) blocks HIV-replication in vitro. CD8+(MHC) class I-restricted cytotoxic T-lymphocytes kill HIV infected cells in tissue culture and may block HIV replication by release of a soluble factor. Reconstitution of immune competence has been done by introducing IL-2 which induced significant nonpermanent increase in the number of CD4 cells. In literature there are some other combinations of IL-2 with glycol or AZT(3-azidothymidine).

Alzheimer's disease, Parkinson's disease and amyotrophic lateral sclerosis, (ALS)

The cause of the neurodegenerative disorders of Alzheimer's disease, Parkinson's disease and amyotrophic leteral sclerosis (ALS) are unknown. It has been proposed that each of these disorders results primarily from a loss of trophic peptidergic neurotransmitter, possible substance P. This loss in turn produces the classical neuronal degeneration seen in each of these diseases and occurs due to a combination of natural aging and chronic autoimmune destruction following viral infection of the CNS early in life. The loss is therefore slow, and by the time of clinical presentation the inflammatory process is disappearing as the antigen stimulus lessens with its removal. (Barker, R., Neuropeptides, 1991 Oct., 20(2))

Other research findings from both clinical investigations and studies of animal models suggest a neuroimmunologic component in age-associated dementia. Clinical studies suggest an association between dementia and brain-reactive autoantibodies in subsets of patients with Alzheimer's disease. Studies in mice suggest that: a)when compared with normal genotypes, mutant mice, with accelerated autoimmunity, show learning and memory impairments at earlier chronological ages; b)the learning and memory deficits of autoimmune and normal mice are qualitatively similar; and c) the behavioral deficits of normal aged and autoimmune mice are sensitive to similar pharmacologic treatment of aging-associated dementia. (Forster, M. J. et al, Brain Research Bulletin, 1990 Sep., 25(3))

There is also clinical proof that even when Parkinson symptoms were not relieved by a month's treatment with L-dopa, they were improved by three weeks administration of corticosteroids. Therefore Nagao et al have proposed autoimmune disease as one of underlying causes for drug-resistant Parkinsonism. (Nagao T. et al, Clinical Neurology, 1991 November, 31(11))

The free radical hypothesis for the pathogenesis of idiopathic parkinsonism (Parkinson's disease) has many similarities to the argument invoking an autoimmune mechanism. In both cases, cellular and molecular machinery that might be involved in neuronal destruction have been demonstrated. In recent years, the free radical hypothesis has become particularly fashionable. Several workers have reported observations which, they infer, support the notion that damage by free radicals is the major factor in the underlying disease process. (Calne, DB, Annals of Neurology, 1992 December, 32(6))

Amyotrophic lateral sclerosis is an idiopathic human degenerative disease of spinal cord and brain motor neurons. According to many articles like (Kimura F et al. Annals of Neurology, 1994 February; Appel SH et al. Journal of the Neurological Sciences 1993 September; Hansen PR et al. Ugerskrift for Laeger, 1991 February) it is in all aspects an autoimmune disease.

Rhamnolipids

The rhamnolipids are a group of glycolipids of biosurfactant activity. Due to different combinations of carbohydrates and lipids, different bonds and different ionic states, there are a variety of glycolipids having a strongly different hydrophilic/lipophilic balance. It is known that various strains of Pseudomonas are capable of extracellular secretion of rhamnolipids, when growing on soluble and insoluble carbon sources.

While rhamnolipids as a class, and various specific rhamnolipid compounds, are known and have been attributed some biological activity, no one to date has suggested the use of rhamnolipids in the treatment of autoimmune diseases and especially no suggestion has been made as to the effectiveness of rhamnolipids on organ specific (or non-specific) autoimmune disease, AIDS, Alzheimer's disease, Parkinson's disease or amyotrophic lateral sclerosis.

Ishigami Y. et al., in the U.S. Pat. No. 4,902,512 disclose-that liposomes, containing rhamnolipids A and B or a salt thereof, are useful as microcapsules for delivery of drugs, proteins, nucleic acids, dyes and other compounds. The only use ascribed to the rhamnolipids within such vesicles is clearly of the auxiliary nature, namely to serve as a tool for various studies and as drug carriers for possible therapeutic purposes.

Wagner et al. disclose in U.S. Pat. No. 4,814,272 a growth promoting effect of rhamnolipid(I) with regard to the ability of P. aeruginosa and some other bacteria to utilize insoluble C-source (n-hexadecane). This effect is associated with the surfactant feature of rhamnolipids. Once present in the growth medium (excreted or added) rhamnolipids would facilitate growing bacteria to emulsify and uptake insoluble hydrocarbons for their growth. The rhamnolipid role in this case was microemulsion formation that would allow diffusion of the hydrocarbon nutrient into microbial cell.

Itoh et al in *J. of antibiotics* 1971.24,(12):855, reported that rhamnolipids might exhibit different biological activities in vitro. They also disclose mycoplasmacidal, antiviral and antibiotic activities of rhamnolipids from different P. aeruginosa strains. The antibiotic activity against some Gram(+) bacteria and Proteus vulgaris was disclosed as more significant with the monorhamnosyl compounds than the dirhamnosyl ones.

Lang at al., in *Fat. Sci. Technol*, 1989,9:363, report antibiotic activities of rhamnolipids tested in vitro. Gram(+) bacteria were inhibited stronger than Gram(−) bacteria as a consequence of different cell wall structures and osmolarities.

Shrypock at al., in *Current Microbiol.* 1984.10:323, disclose that Pseudomonas rhamnolipid stimulates both chemotaxis (directed migration) and chemokinesis (enhanced random migration) of leukocytes. At higher concentrations leukocytes would be lysed, expressing hemolytic feature of rhamnolipids. Tests were done with regard to cystic fibrosis caused by P. aeruginosa strains, with the prediction of some importance in host-parasite interactions.

Japanese patent No. 63 253 025 discloses a rhamnopyranosyldecanoic acid as an active ingredient in an anti-inflammatory composition applied orally or parenterally. Its effect is based upon phospholipase A2 inhibition.

Derwent abstract No. 85-272338 mentions an emulsifying composition containing, among others, a glycolipid that could be useful for cosmetics, medicine and foods. No rhamnolipid has been mentioned as having any pharmacological activity within such a composition.

Hirayama et al., in *Febs Letters* 1982.139,1:81. disclose novel methyl-rhamnolipids isolated from P. aeruginosa as biologically active compounds with antibacterial, mycoplasmacidal, and antiviral activities.

German patent DD, A, 248 279 relates to the posibility of antiphytoviral therapy against, for instance, potato -X-virus, or tobacco-mosaik-virus.

In German patent DE-A-2 150 375, antibiotic activity against Bacillus subtilis is mentioned as well as biological activity against mycoplasma.

Haferburg et al. in Acta Biotechnologica 7, No.4, 1987, p 353, show that a rhamnolipid from P. aeruginosa 196 A reduces the number of local legions of tobacco mosaic virus on leaves of the hypersensitive host Nicotiana glutinosa L. by up to 90%. To a similar degree, red clover mottle virus was also influenced by rhamnolipid.

In Belgian patent no. 1,005,704, Piljac G. et al., disclose topical application of rhamnolipids for the treatment of psoriasis and related dermatological diseases.

In Belgian patent no. 1,005,825, Piljac G. et al., disclose possible application of rhamnolipids in different industries based upon its surface tension and interfacial tension activities.

SUMMARY OF THE INVENTION

Accordingly, one subject of the present invention is to provide a method for treating an autoimmune disease by administering a composition containing, as the active ingredient, one or more rhamnolipids.

A further object of the present invention is to provide a method for providing immunorestoration to a subject in need thereof using a composition having one or more rhamnolipids as the active ingredient.

Another object of the present invention is to provide a method for immunomodulation of the immune system in a subject in need thereof using a composition having one or more rhamnolipids as the active ingredient.

Another object of the present invention is to provide a method for treating organ specific and organ non-specific autoimmune diseases using one or more rhamnolipids as the active component in treatment.

Another object of the present invention is to provide a method for treating AIDS by administration of one or more rhamnolipids to a subject in need thereof.

Another object of the present invention is to provide a method for treating Alzheimer's, Parkinson's Disease or amyothropic lateral sclerosis by treatment with a composition containing one or more rhamnolipids as the active ingredient.

These and other objects of the present invention have been satisfied by the discovery that rhamnolipids of formula (I)

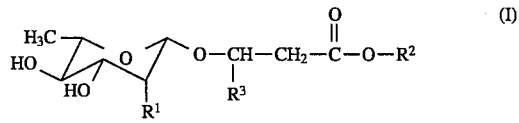

wherein

R$^1$ is H or α-L-rhamnopyranosyl;

$R^2$ is H or —CH($R^4$)—CH$_2$—COOH;

$R^3$ is (C$_5$–C$_{20}$)-saturated, mono or polyunsaturated hydrocarbyl; and $R^4$ is (C$_5$–C$_{20}$)-saturated, mono or polyunsaturated hydrocarbyl provide immunological activity and are effective at immunorestoration and immmunomodulation, thus providing effective treatment of organ specific and organ non-specific autoimmune diseases, AIDS, Alzheimer's disease, Parkinson's disease, and amyothropic lateral sclerosis.

DETAILED DESCRIPTION OF THE PREFERRED EMBODIMENTS

The present invention relates to methods for treating various autoimmune diseases by administering, to a subject in need thereof, an effective amount of a composition comprising, as active ingredient, one or more rhamnolipids of formula (I)

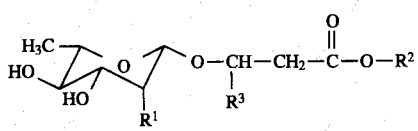

(I)

wherein $R^1$ is H or α-L-rhamnopyranosyl;

$R^2$ is H or —CH($R^4$)—CH$_2$—COOH;

$R^3$ is (C$_5$–C$_{20}$)-saturated, mono or polyunsaturated hydrocarbyl and $R^4$ is (C$_5$–C$_{20}$)-saturated, mono or polyunsaturated hydrocarbyl.

In the composition used in the methods of the present inventions, the rhamnolipid which is preferred is a di-rhamnolipid (r'=α-L-rhamnopyranosyl).

Further, when the $R^2$ substituent is H, the rhamnolipid contains only one lipid group, whereas when $R^2$ is —CH($R^4$)—CH$_2$—COOH, the rhamnolipid has 2 lipid units coupled by an ester linkage.

Substituents $R^3$ and $R^4$ may be straight, chained or branched C$_5$–C$_{20}$ hydrocarbon groups, which may be saturated or contain one or more unsaturation sites. Preferred are linear saturated alkyl groups of formula —(CH$_2$)$_x$—CH$_3$, with x=4–20. Most preferably, X=4–6 for the linear saturated alkyl groups.

A most preferred embodiment of rhamnolipid is the compound of formula (II) below:

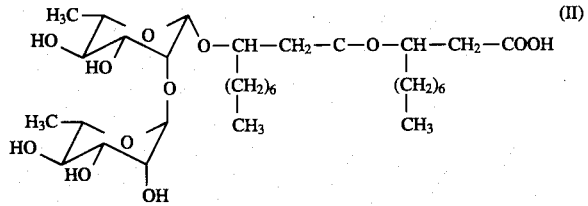

(II)

Bacteria capable of synthesizing the rhamnolipids of the present invention can be isolated from oil well drilling mud, which have been found to contain bacteria which produce rhamnolipids when the bacteria are grown on either a soluble carbon nutrient source (glucose) or an insoluble carbon nutrient source (glycerol, gas oil). A suitable bacterium has been isolated and characterized as Pseudomonas aeruginosa.

In treating autoimmune diseases in accordance with the methods of the present invention, a pharmaceutical composition having, as active ingredient, one or more of the rhamnolipid of formula I, is administered to a subject in need thereof. Of the various autoimmune diseases, the methods preferably provide treatment for organ specific and organ non-specific autoimmune diseases with the diseases of psoriasis, lichen ruber planus, systemic lupus erythematosus, ichtyosis, AIDS, Alzheimer's disease, Parkinson's disease and amyotrophic lateral sclerosis being the most preferred diseases for treatment.

The pharmaceutical composition can be administered in any conventional manner, including but not limited to, orally, intravenously, intraperitoneally and dermally. Dosages depend on the weight of the subject being treated and can be readily determined by one of ordinary skill in the medicine given the LD$_{90}$, LD$_{50}$, LD$_{10}$ and single lethal dose values, as well as single dose toxicity (one dose per day), day), 5 doses toxicity (5 doses per 5 days, 1 dose per day) and 5 doses toxicity (5 doses per day). For the present rhamnolipid the dosage range is from 4.0 mg/kg to 13.0 mg/kg, with dosages of from 4.5 mg/kg to 12.5 mg/kg preferred, and dosages of from 6.5 mg/kg to 11.5 mg/kg most preferred. The curing dosage for an adult human is approximately 100 mg/day to 1000 mg/day.

The pharmaceutical composition may be as a liquid suspension in water, a cream or lotion, as an injectable solution in water or as a solid formed into a capsule or tablet with standard capsule or tablet forming excipients common in the pharmaceutical field. If the composition is administered orally, within solution (or suspension) form or as a capsule or tablet, it may be desirable to include in the composition suitable buffering agents conventional in the art of pharmaceuticals to allows protection in the gut of the subject being treated and to avoid stomach upset of the subject.

The data provided in the Examples section below provide both a general pharmacological profile of the rhamnolipids of the present invention, with particular attention to rhamnolipid (II), and data directed to the efficacy of the rhamnolipids in treatment of autoimmune disease.

The in vitro results which relate specifically to treatment of autoimmune disease include data on inhibition of enzymes selected from lipoxygenase, acetylcholinesterase, beta galactosidase, carboxypeptidase A and trypsin, and the effect of the rhamnolipids on DNA synthesis, cell cytotoxicity, T-lymphocyte proliferation and T-lymphocyte proliferation with ConA.

The in vivo data which relate specifically to treatment of autoimmune disease include the effects of the rhamnolipids on cellular immunosuppression: oxazolone induced delayed type hypersensitivity, immunorestoration: immunosuppression with cyclophosphamide and infection with Candida, and immunomodulation: infection with Candida albicans.

Also included below are clinical data on the treatment of several dermatological autoimmune diseases which show excellent curative effects for the rhamnolipids of the present invention when compared to conventional therapy using corticosteroids against the art-recognized autoimmune diseases of Psoriasis and Lichen ruber planus.

In vitro tests of alpha-L-rhamnopyranosyl-(1,2)alpha-L-rhamnopyranosyl)-3-hydroxydecanoyl-3-hydroxydecanoic acid (rhemnolipid II) on enzyme inhibition, shows the following enzymes were inhibited in various concentrations:

lipoxygenase 10 ug/ml acetylcholinesterase 1 mg/ml alpha-amylase 1 mg/ml beta-galactosidase 100 ug/ml carboxypeptidase A 1 mg/ml trypsin 1 mg/ml The rhamnolipids of the present invention show only weak inhibitory effects on p56 $^{1ck}$ Tyrosine kinase at the concentration of 100 uM (11% inhibition), as well as on p59$^{fyn}$ Tyrosine kinase at the same concentration (15% inhibition). No activity has been observed against the following enzymes: alpha-chymotrypsin, papain, elastase, alpha-glucosidase, alcalinephosphatase, leucineaminopeptidase, and adenosinedeaminase.

The present rhamnolipids, at the concentration of 0.1 mg/ml, in the absence of serum growth factors, show a inhibition of DNA synthesis in A 431 cells, with total inhibition by rhamnolipid II. The rhamnolipids of the present invention worsen the cell "suppressive" effects of phorbolmyristate-acetate (PMA), protein kinase C activator (PKC), already noticeable at 0.05 mg/ml. The Ames test was negative for rhamnolipid II of the present invention. Functional assays of B-cell proliferation, without lipopolysaccharide do not show any sign of stimulation or suppression, while significant suppression of B-cell proliferation in the presence of added lipopolysaccharide, is found using a concentration of 10 uM and 1 uM for rhamnolipid II. T-cell proliferation is inhibited in the presence of 10 uM of rhamnolipid, of the present invention with and without Con A. In the presence of 100 uM of rhamnolipid, Dopamine $D_1$ (human recombinant) [$^3$H] SCH23390 receptor and Dopamine $D_{2A}$ (human recombinant) [$^3$H] spiperone receptor are each inhibited, with rhamnolipid II providing 101% inhibition of the dopamine D, receptor and 53% of the dopamine $D_{2A}$ receptor.

The rhamnolipids of the present invention, four days after intravenous administration at a concentration of 7.5 mg/kg, show a significant increase in neutrophils and a decrease in lymphocytes in vivo in mouse. The same results are seen after 29 days following administration of the rhamnolipids.

Immunopharmacological test results show no cellular immunostimulation by the present rhamnolipids based on oxazolone-induced delayed type hypersensitivity, while cellular immunosuppression test of oxazolone-induced delayed type hypersensitivity shows a moderate immunosuppression activity of the rhamnolipids. Humoral immunostimulation and immunosupretion tests do not show any significant activity. An immunomodulation test of the present rhamnolipids, based on infection with Candida albicans, shows moderate activity, in the range of 10 mg/kg and 1 mg/kg for rhamnolipid II. An immunopharmacological test, based on immunosuppression with cyclophosphamide and infection with *Candida albicans,* shows very strong immunorestoration activity using the rhamnolipids of the present invention, even at a concentration of 10 mg/kg or higher and moderate immunorestauration with intraperitoneal doses, even at a concentration of 0.1 mg/kg.

Upon IV administration of the rhamnolipid II, the average $LD_{50}$ for a mouse was found to be 105.0 mg/kg. The micronucleus test in vivo on chromosomal structural aberrations in red bone marrow cells shows that a concentration of described rhamnolipid of 31.5 mg/kg of the animal body weight, does not cause any malfunctions in chromosomes nor chromatides in comparison with a control group.

Because there is strong evidence in the scientific literature that Alzheimer's disease, Parkinson's disease and amyothropic lateral sclerosis are autoimmune diseases, the therapy of such illnesses should be targeted towards the curing of immunological malfunctions. This indicates that drugs applied, should have proven immunosuppression, immunomodulation and immunorestoration activity. AIDS is also an autoimmune deficiency disease. Accordingly, many new approaches towards AIDS treatment include immunoreconstitution and blocking of viral entry into the T cells.

The present rhamnolipid (II) at a concentration of 10 umol/kg, showed in vitro T cell immunosuppression activity with or without stimulation with ConA. It showed moderate in vivo immunomodulation activity and very strong in vivo immunorestoration activity. In clinical trials on dermatological autoimmune diseases like psoriasis, rhamnolipid (II) at 1% concentration showed long-lasting curative effects in comparison with corticosteroids. Even more, some patients are still in remission of the treated area after three years.

The same rhamnolipid showed inhibition activity on different enzymes which have specific tasks in autoimmune diseases, Alzheimer's, Parkinson's, and AIDS. Lipoxygenase inhibitors (Chen. F. et al. Ophthalmic Research, 1991) have a significant influence in suppressing development of experimental autoimmune uveitis. Spurney R. F. et. al. (Kidney International, 1991 January) have shown that increases in leukotriene production within the kidney may be important in the pathogenesis of lupus nephritis.

According to Eisenlohr, LC et al. (Cell, 1992 December) expression of the membrane caroxypeptidase A enhances presentation of certain endogenously synthesized peptides to MHC class I—restricted cytotoxic T-lymphocytes. Therefore, inhibition of carboxypeptidase A is important to prevent expression of peptides to MHC class I—restricted cytotoxic T-lymphocytes.

Wall, JR et al. (Journal of Endocrinological Investigation, 1993 December) disclose a fusion protein with beta galactosidase which was detected in 29–43% of patients suffering from thyroid-associated ophthalmopathy, Graves' hyperthyroidism and in patients with untreated Hashimoto's thyroiditis. Inhibition of beta galactosidase can prevent creation of this fusion protein.

Inhibition of acetylcholinesterase is a well known way to find new drugs against Alzheimer's disease. Cacabelos, R et al (Annals of the New York Academy of Sciences, 1993, September), have proposed that the cholinergic dysfunction present in Alzheimer's disease might be due to a specific vulnerability of cholinergic neurons linked to neurotrophic imbalance, neuroimmune impairment, and/or direct effects of beta-amyloid deposition and NFT (neurofibrillary tangles) formation in acethylcholine neurons. According to this hypothesis, a multifactorial treatment of Alzheimer's disease should produce: 1) inhibition of beta-amyloid and NFT formation; 2) restoration of neuronal membrane integrity; and 3) control of neuroimmune auto-aggression.

Gabuzda, D et al. (Journal of Neurochemistry, 1993 December) have proposed that protein kinase C activation (PKC activation) inhibits beta-amyloid production. As it was shown in tissue culture on human A431 epidermal cells, rhamnolipid (II) of the present invention worsened the cell "suppressive" effects of phorbol-myristate-acetate (PMA), protein kinase C activator, already noticeable at 0.05 mg/ml. Therefore it is likely that rhamnolipids of the present invention are also PKC activators. Therefore, they will prevent beta-amyloid production in humans.

Kozaki, Y. et al. (Biological and Pharmaceutical Bulletin, 1993 April) showed that trypsin inhibitors also strongly inhibit the tryptase activity of HeLa cells. A membrane-bound tryptase TL2 binds specifically to the external envelope protein gp120 of HIV-1, interacting with its V3 domain. The binding was selectively blocked by inhibitors of tryptase TL2 (Kido, H et al; Febs letters, 1991 July). This trypsin-like proteinase is inhibited by recombinant gp120 of HIV coat. As these envelope glycoproteins play a crucial role when HIV binds to and enters target cells, inhibition of a membrane-associated proteinase, as a complementary or alternative receptor to the CD4, will prevent the virus in entering the host cells and prevent the spreading of HIV infection. Therefore, inhibitors of trypsin such as the rhamnolipids of the present invention will prevent binding to trypsin-like proteinase on the human T4-lymphocytes.

In the Belgium patent No. 1,005,704, the present inventors showed, through clinical data a strong activity in the treatment of autoimmune diseases, like Psoriasis and Lichen rubber planus when 1% rhamnolipid ointment was applied. In the same patent the activity on other autoimmune diseases like Pemphygus vulgaris, ichtyosis and Lupus erythematosus systematicus was postulated as well.

According to the results provided herein, which show that the rhamnolipids of the present invention have very distinct inhibitory activity on various enzymes which are responsible for the development of certain autoimmune illnesses, and have very potent immunological activity, especially immunorestoration, as well as clinical proofs on dermatological autoimmune diseases, it follows that a pharmaceutical composition comprising as active ingredient one or more rhamnolipids, is effective in the treatment of described organ specific and non-specific autoimmune diseases: AIDS, Parkinson's diseases, Alzheimer's disease and amyothropic lateral sclerosis.

Having generally described this invention, a further understanding can be obtained by reference to certain specific examples which are provided herein for purposes of illustration only and are not intended to be limiting unless otherwise specified.

EXAMPLES

Strain characteristics

From oil well mud, using selective media, a rod shaped Gram (−) bacterium capable of rhamnolipid biosurfactant excretion was isolated. Applying BBL$^R$ Minitek™ Numerical Identification System, Instructions for nonfermentors and miscellaneous Gram (−) bacteria (BBL$^R$ Microbiology Systems; 1987) this bacterial strain was determined as Pseudomonas aeruginosa having Type number:646011. Besides the reactions that provided the above profile number for numeric identification, the following growth tests were also performed:

| TESTS | RESULTS |
| --- | --- |
| Oxidase | + |
| Anaerobic dextrose | − |
| Aerobic dextrose | + |
| Maltose | − |
| Saccharose | − |
| D-xylose | + |
| Arginine dihydrolase | + |
| Lysin decarboxylase | − |
| Ornithine decarboxylase | − |
| Urease | − |
| ONPG | − |
| Indole | − |
| Citrate as the single carbon source | + |
| Reduction of nitrate in nitrite | − |
| Denitrification (N2) | + |
| Starch hydrolysis | − |
| Phenylalanine deamination | − |
| Growth on: Mac Conkoy plate | + |
| SS plate | + |

The maximal temperature at which growth still occurs was 45° C., when exposed for 24 h. The maximal NaCl tolerance, at which growth still occurs was 9%, when exposed for 24 h.

Rhamnolipid production and isolation

A producing strain of P. aeruginosa was cultivated aerobically, at 28°–32° C. semi-continuously (RFBC) in 15L (LKB) bioreactors, or using a batch procedure in a 30L fermentor (Electrolux). Aeration for the RFBC procedure was 2.0–3.0 1/min, vortex mixing was 400–8,000 rpm and the working volume of bioreactor, because of the foam, never exceeded ⅔ of the total bioreactor volume; (4.5–7.1L for LKB fermentor). The batch procedure was operated at an aeration of 5.0–30.0 1/min in the 30L fermentor, applying vortex mixing at 600–1,000 rpm and a working volume of 12 L with an Electrolux fermentor.

During batch production, the initial concentration of glucose was 9.0 g/l, decreasing to the 2.0–2.5 g/l after 15–20 h of cultivation and dropped to the 1.5–2.0 g/l while approaching the end of cultivation. Inoculum for the bioreactor was grown for 48 h in 500 ml flasks (100 ml medium) on the Brown rotary shaker (240 rpm) and such prepared inoculum was added to a medium in fermentor in an amount of 5%.

In the semi-continuous cultivation process, the process was started and maintained as a batch procedure for 24 h, during which time glucose concentration would drop to 2.0 g/l and then a fresh cultivation medium had to be added at a rate of 3.0 1/8 h. Every 8 h, 3.0 L of spent broth was withdrawn (or every 4 h, 1.5 L was withdrawn). Glucose concentration was variable between 2.0 g/l and 4.5 g/l. The bioreactor was inoculated with 5% of the above described inoculum. The cultivation temperature in both procedures was 32° C.

The pH was monitored automatically by pH electrodes, surface tension was measured by White's ring-tensiometer, biomass increase was measured spectrophotometrically by Horizon digital colorimeter at 610 nm and glucose uptake by the same instrument at 490 nm.

The cultivation medium was composed of: 9 g glucose, 5 g peptone, 2 g yeast extract, 5 g NaCl, 0.5 g $K_2HPO_4$, 0.5 g $KH_2PO_4$, 2 g $MgSO_4$, $H_2O$, 3 g $KNO_3$, 1 ml Gottlib solution and 1 liter water. Much better yield could be obtained if glucose was substituted with glycerol as a carbon source, creating consequently a two phase system. An alternate medium was: 0.5 g $K_2HPO_4$, 0.5 g $KH_2PO_4$, 0.2 g $MgSO_4$, 2 g $KNO_3$, 1 g NaCl, 1 ml Gottlib solution, $1LH_2O$ and 3% of insoluble carbon source (glycerol, gass oil). Decrease of the surface tension (28–31 mN/m) was used as an indicator of the yield and the end of fermentation.

Rhamnolipid purification and isolation

Concentration

After fermentation, biomass was separated in a continuous flow Sharples centrifuge at 60,000 G and room temperature. The obtained supernatant was than processed as described below.

The initial volume was reduced by evaporation to ⅒ of the original volume and then acid precipitated by conc. HCl at pH 1.5–2.0 and +4° C. Extracellular glycolipids, which are readily soluble in water, could be easily concentrated by altering pH and temperature during the acid precipitation. The filter pellet was than redissolved in water and subjected to ultrafiltration over a 0.1 mm filter, $10^6$ and $10^5$ filter (PTHK000C5) with a Millipore continuous flow system. Rhamnolipids could be concentrated by ultrafiltration because they form micelles at concentrations above the critical micelle concentration, allowing these aggregates to be retained by relatively high molecular weight cut-off membranes. Lower molecular weight impurities such as salts, free amino acids, peptides and small proteins were thus easily removed. This method is very important in rhamnolipid purification as large volumes of media can be processed rapidly at extremely low cost.

Good concentration could be achieved also by solvent extraction, for example, very successfully with dichloromethane. A further purification step could then be performed later on in the processing by doing a $CH_2Cl_2$ extraction after acid precipitation.

Chromatography

Column chromatography

Column chromatography was done on a low pressure lab scale and preparative (Pharmacia) adsorption onto Amberlite XAD-7, XAD-8 resin (Rohm&Haas). Equilibration and rinsing was done with water and rhamnolipids were eluted with up to 50% of EtOH or MeOH. Organic solvent was later evaporated and rhamnolipid fractions acid precipitated. Anion exchanger IRA-400 (Cl-cycle) could be also used, but was less convenient because of elution with 1 M NaCl.

Preparative HPLC was done with a Waters instrument and silica columns. Acid precipitated and lyophilized rhamnolipids were dissolved (10 g/50 ml) in propanol and loaded onto a silica (500 ml) column equilibrated with hexane. Active fractions were eluted with propanol-25% NH$_4$OH (4:1), organic solvent was evaporated and pure rhamnolipids were again acid precipitated, redissolved in water, pH adjusted to 7.2 with 0.1 N NaOH and lyophilized for safe storage.

Thin layer chromatography of specimens

Fractionated supernatant of the culture broth, acid precipitate, dichloromethane extracts, twice purified precipitate and different fractions in the process of purification were submitted to thin layer chromatography on silica-gel 60 F 254 (Merck) 0.2–0.5 mm, and preparative plates, prepared with the same carrier (Kemika), 2 mm thick. Plates (0.2 ml wide) were activated in the dryer for 1 hour at 90° C. and used in the next 30 min. Specimens were developed in the solvent mixture of propanol and 25% NH$_4$OH in the ratio 80:15. Sample quantity, loaded on the plates, depended of the type and purity of the samples. Average Rf value was 0.26 after 3 hours running time.

For the purposes of visualization and chemical detection of the specimens, spray reagents, prepared according to Merck Dying Reagent for Thin Layer and Paper Chromatography (1980) CRC-Press Handbook of Chromatography, Volume II (1972) and M. Kates, Techniques of lipoidology (1972), were used. Alpha-naphthol and diphenylamine as reagents for glycolipid detection were preferred.

Spectral analysis and rhamnolipid structure

Spectral analysis

After thin layer chromatography the preparations were identified using $^1$H NMR, $^{13}$C NMR and mass spectrophotometry. Some data are shown below.

| $^{13}$C-NMR(75 MHz; DMSO-d6) | | | | | |
|---|---|---|---|---|---|
| C | ppm | C | ppm | C | ppm |
| 1" | 97.7 | 1 | 173.3 | 1' | 170.6 |
| 2" | 77.3 | 2 | 40.8 | 2' | 40.2 |
| 3" | 70.4$^a$ | 3 | 72.2$^a$ | 3' | 71.4$^a$ |
| 4" | 73.2 | 4 | 33.7 | 4' | 32.5 |
| 5" | 68.9 | 5 | 24.8 | 5' | 24.1 |
| 6" | 17.9 | 6 | 28.8–29.2 | 6' | 28.8–29.2 |
| 1''' | 102.2 | 7 | 28.8–29.2 | 7' | 28.8–29.2 |
| 2''' | 70.4$^a$ | 8 | 31.4 | 8' | 31.4 |
| 3''' | 70.8$^a$ | 9 | 22.2 | 9' | 22.2 |
| 4''' | 72.4 | 10 | 14.0 | 10' | 14.0 |
| 5''' | 68.8 | | | | |
| 6''' | 17.8 | | | | |

| $^1$H-NMR(300 MHz, DMSO-d6) sugar part | | |
|---|---|---|
| H | ppm | |
| 1"; 1''' | 4.8; 4.9 | 2x singlet (2H) |
| 2"; 2''' | | |
| | 3.20→4.10 | multiplet (8H) |
| 5"; 5''' | | |
| 6"; 6''' | 1.21 | doublet, J=5.9Hz(6H) | lipid part

| H | ppm | |
|---|---|---|
| 2.2' | 2.43, 2.53 | 2x doublet, J=6.0Hz(4H) |
| 3.3' | 3.20–4.1 | multiplet (2H) |
| | 5.24 | multiplet (2H) |
| 4.4' | 1.6 | multiplet (4H) |
| 5.5'→9.9' | 1.3 | multiplet (16H) |
| 10.10' | 0.97 | triplet, J=6.3Hz(6H) |

Mass spectra m/z: 673 [M + H + Na]$^+$
m/z: 695 [M + H + 2Na]$^+$
m/z: 525 [M − C$_{10}$H$_{18}$O$_2$ + 2Na]$^+$ minus terminal lipid
m/z: 379 [m − C$_{10}$H$_{18}$O$_2$ − rhamnose + 2Na]$^+$ minus terminal lipid and rhamnose note:
$^a$assignments may be reversed Rhamnolipid structure From the spectral data, the rhamnolipid has been identified as (alpha-L-rhamnopyranosyl-(1,2)alpha-L-rhamnopyranosyl)-3-hydroxydecanoyl-3-hydroxydecanoic acid, having the following structure:

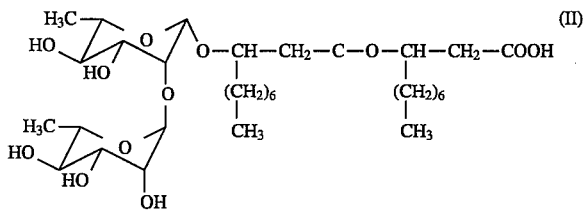

(II)

The in vitro and in vivo tests were performed using purified (II).

IN VITRO TESTS

Enzyme inhibitions

Rhamnolipid (II) was tested in vitro against a wide array of enzymes.

The following enzymes were inhibited at the various rhamnolipid concentrations indicated:

lipoxygenase 10 ug/ml acetylcholinesterase 1 mg/ml alpha-amylase 1 mg/ml beta-galactosidase 100 ug/ml carboxypeptidase A 1 mg/ml trypsin 1 mg/ml All enzyme assays were done spectrophotometrically by computer linked automatic microplate reader (Labsystem Multiskan) and Diode Array spectrophotometer (Perkin Elmer).

TABLE 1

| Solvent: 0.5% DMSO | Conc. | % inh. |
|---|---|---|
| P561ek Tyrosine Kinase | 100 μM | 11 |
| | 1" | 3 |
| | 0.01" | 4 |
| P59fyn Tyrosine Kinase | 100 μM | 15 |
| | 1" | 0 |
| | 0.01" | 1 |
| Dopamine D1 (human recombinant) | 100 μM | 101 |
| [$^3$H] SCH23390 | 1" | 8 |
| | 0.01" | 8 |

Rhamnolipid (II) was found to have no effect on the following enzymes:

alpha-chymotrypsin papain elastase alpha-glucosidase alkalinephosphatase

Effect on viruses

Tests were performed according to D. A. Vanden Berghe et al., Inst. Pasteur 84,101 (1986). Rhamnolipid (II) was toxic for VERO cells in concentrations ≧200 ug/ml, and cytotoxic on MT4 cells in concentrations >169.40 ug/ml. It had no activity against:

herpes simplex virus coxsackie B2 virus measles edmonston A virus polio I virus semliki forest virus vesicular stomatitis virus, in concentrations ≦100 ug/ml Against HIV I, strain IIIB, Rhamnolipid II gave a maximal protection of only 9%.

Antibacterial activity of rhamnolipid (II)

The Minimum inhibitory concentration (MIC) of Rhamnolipid II for *Candida albicans, Escherichia coli, Staphylococcus aureus* and *Pseudomonas aeruginosa* was >0.5 % in tested medium.

Effect on cell DNA synthesis and cell cytotoxicity Rhamnolipid (II) completely inhibited DNA synthesis in A431 human epidermal cells at a concentration of 0.1 mg/ml, in the absence of serum growth factors (Table 2). At a concentration of 0.5 mg/ml, in the presence of serum, rhamnolipid (II) was found to be cytotoxic to the cell (Table 3). The same rhamnolipid worsened the cell "suppressive" effects of phorbol-myristate-acetate (PMA), protein kinase C activator (PKC), already noticeable at 0.05 mg/ml. Thus, rhamnolipid (II) suppressed A431 cell growth in particular in the presence of PMA. This suggests favorable "keratinocyte" inhibitory action in the rhamnolipid preparation of the present invention. The synergistic action of the present rhamnolipid with PMA makes it unlikely that rhamnolipid (II) is a PKC inhibitor.

At the same time rhamnolipid (II) showed no effect on basal tissue plasminogen activator (t-PA) released by human umbilical cord venous endothelial cells. The t-PA released, induced by PMA, was slightly inhibited at 0.1 mg/ml, but this concentration was also cytotoxic to the endothelial cells.

Collagen induced platelet aggregation in rat platelet rich plasma was not affected by rhamnolipid (II) at 0.1 mg/ml. Thus, no interference was seen with the cell activation system as it occurs in rat platelets (includes PKC).

TABLE 3

Effect of rhamnolipid on A431 call DNA synthesis

| Rhamnolipid [mg/ml] | DNA synthesis [³H] Thy inc. [dpm] | % placebo |
|---|---|---|
| Serum free medium | | |
| 0 | 7606 +/− 3109 | 100 +/− 41 |
| 0.001 | 6935 +/− 2432 | 91 +/− 32 |
| 0.01 | 4885 +/− 1480 | 64 +/− 19 |
| 0.1 | 134 +/− 129 | 2 +/− 2 |
| 10(v/v)% FCS | | |
| 0 | 33362 +/− 5159 | 100 +/− 15 |
| 0.001 | 35400 +/− 2786 | 106 +/− 8 |
| 0.01 | 31273 +/− 2028 | 94 +/− 6 |
| 0.1 | 37055 +/− 1881 | 111 +/− 6 |

A431 cells were cultured for 24 h in microtitter platesm, with serum free medium or in the presence of serum with rhamnolipid. Then, [³H] thymidine was added and cells were harvested after 48 h; [³H] incorporated into DNA was determined.

TABLE 4

Effect of rhamnolipid on A431 cell cytotoxicity

| Rhamnolipid [mg/ml] | Cell viability [MTT conversion, ΔE540] | % placebo |
|---|---|---|
| 10(v/v)% FCS, 24 h + PMA 10⁻⁸M | | |
| 0 | 100 +/− 21 | 93 +/− 17 |
| 0.02 | 124 +/− 4 | |
| 0.05 | 132 +/− 3 | 62 +/− 3 |
| 0.17 | 96 +/− 5 | 57 +/− 19 |
| 0.5 | 0 +/− 0 | 2 +/− 4 |
| 10(v/v)% FCS, 48 h + PMA 10⁻⁸M | | |
| 0 | 100 +/− 21 | 52 +/− 4 |
| 0.02 | 143 +/− 8 | |
| 0.05 | 141 +/− 15 | 53 +/− 0 |
| 0.17 | 120 +/− 3 | 33 +/− 2 |
| 0.5 | 0 +/− 0 | 7 +/− 10 |

To determine rhamnolipid cytoxicity, A431 cells were incubated with rhamnolipid, in the presence of serum, for 24 h or 84 h after which mitochondrial MTT conversion capacity was determined. Mitochondial MTT conversion capacity is an accepted marker for cell viability.

Ames test

Tests were performed according to the method described by Ames N. Bruce et al. (Mutation Research, 31 (1975), 347–364). Test concentrations of rhamnolipid (II) were 10, 100, 200, 500, 1000 ug/plate.

In the range of tested rhamnolipid concentrations, the number of bacterial revertants per Petri dish was in the range of spontaneous revertants which are present without S9 mixture. Therefore, it can be concluded that Rhamnolipid (II) was not mutagenic at the tested concentrations.

Mutagenicity tests in tissue culture

Plating efficiency determination and generation time. Tests were performed on CHO cell line. The generation time (GT) and plating efficiency (PE) was determined to be as follows.

GT=16 hours

PE=90%

Population growth of CHO cell culture

Population growth of asynchronous cell culture (CHO cells), was performed in accordance with Freshney R. Ian: "Culture of animal cells", 1983; (125–128) The following concentrations of rhamnolipid: 31.25 ug/ml, 62.50 ug/ml, and 125.0 ug/ml, were added to a growth medium of CHO cells. With regard to the applied rhamnolipid concentrations, the proliferation ability of CHO cells was not significantly changed.

Colony forming ability

The colony forming ability of CHO cells after treatment with various concentrations of rhamnolipid (II) was performed in accordance with Kilbey B. J. et al.: "Handbook of mutagenicity test procedures", 1977; (68 and 175). The following concentrations of rhamnolipid (II) were tested: 0, 8, 16, 32, 62.5 and 125 ug/ml. Compared to the control group there was no significant loss of colony forming ability observed at the cited concentrations of rhamnolipid (II).

Structural chromosomal aberration analysis

Structural chromosomal aberrations analysis (Biological Dosimetry 1986, Technical; Reports Series, 20, International Atomic Energy Agency, Vienna, pp. 59.) Different concentrations of rhamnolipid (II) were administered at 2 h and 16 h ( 31.25, 62.50, 125 and 250 ug/ml). 400 of the metaphases were clearly observed and 20 chromosomes (aneuploid) were analyzed per each specimen. It was evident that the concentration of 31.25 ug/ml caused a larger number of structural chromosomal aberrations when compared to the untreated control specimen. The concentration of 62.50 ug/ml in the same incubation time decreased the tendency of chromosomal aberrations, while for the largest two concentrations the values were almost the same as in the control group. A significantly different situation was observed after 16 h incubation time with test substance. Overall structural chromosome damages increased several fold, as well as the number of cells with 2 to 4 aberrations. However, in this case as well, it is interesting to note that the number of aberrations decreased as the concentration increased.

The phenomenon, of so called defect of spiralization, was not observed after 2 hour incubation of CHO cells with rhamnolipid (II).

Micronucleus test

Micronucleus test (Adapted method from: *French M. and A. A. Morley* (1986) Mutation Res., 161:193.) Results of the micronucleus test with rhamnolipid (II) concentrations of: 31.25 ug/ml, 62.50 ug/ml, 125 ug/ml and 250 ug/ml clearly showed the interaction of the tested compound and intracellular content. Micronuclei numbers increased compared to the parallel control specimens. After 16 h incubation of CHO cells with rhamnolipid, the number of micronuclei inside certain binuclear cells increased up to 4.

Sister chromatide exchange analysis

This method was adapted from: Kato H., Nature (1974) 252:70. The test concentrations of rhamnolipid (II) were as follows: 31.25 ug/ml, 62.50 ug/ml, 125 ug/ml and 250 ug/ml. Results of this method did not show significant differences between control and treated cultured cells.

Chronic exposition of CHO cells to rhamnolipid.

The method was adapted from Kilbey B. J. et all.:"Handbook of mutagenicity test procedures", 1977:250 and 267. After 30 of repeated 2 h or 16 h exposures of the CHO cells to rhamnolipid (II) concentrations: 31.25 ug/ml, 62.50 ug/ml, 125 ug/ml, the overall frequency and type of chromosomal aberrations did not significantly differ from the control samples.

Hemolytic activity

Hemolytic activity of rhamnolipid (II) could be seen after sedimentation of erythrocytes, when hemoglobin colored the solution. If there was no hemolytic activity, erythrocytes would have precipitated without coloring the solution. For test purposes 1 ml of citrate bovine blood was added to 49 ml of isotonic solution.

Series of test samples were prepared in concentrations ranging from 1.0 mg/ml to 0.01 mg/ml. 1 ml of diluted citric bovine blood was added to 1 ml of diluted test sample. The test tube was gently mixed and left for 0.25 h, 1 h and 24 h, respectively. The lowest dose of rhamnolipid II that caused hemolysis in 15 min. was 0.35 mg/ml; in 1 h was 0.25 mg/ml and in 24 h was 0.125 mg/ml.

TABLE 4

Hemolytic activity

| Dilution | Sample 1 | Sample 2 |
| --- | --- | --- |
| 0.500 mg/ml + | 15 min. + | 15 min. |
| 0.375 mg/ml + | 15 min. + | 15 min. |
| 0.350 mg/ml + | 15 min. + | 15 min. |
| 0.300 mg/ml + | 1 hour + | 1 hour |
| 0.250 mg/ml + | 1 hour + | 1 hour |
| 0.200 mg/ml + | 24 hours + | 24 hours |
| 0.150 mg/ml + | 24 hours + | 24 hours |
| 0.125 mg/ml + | 24 hours + | 24 hours |
| 0.100 mg/ml − | − | |
| 0.075 mg/ml − | − | |
| 0.050 mg/ml − | − | |
| 0.005 mg/ml − | − | |

TABLE 4-continued

Hemolytic activity

| Dilution | Sample 1 | Sample 2 |
| --- | --- | --- |

CONCLUSION:
0.25 mg of rhamnolipid (II) diluted in 2 ml isotonic solution of diluted citric bovine blood led to hemolytic activity. Lower concentrations did not.

Lymphocyte proliferation tests

B-lymphocyte Proliferation

Procedure: B-cells were isolated from mouse spleens using conventional procedures, and suspended in DMEM. $10^6$ cells/ml were incubated overnight at 37° C. to assess stimulation (positive score, related to 1 ug/ml lipopolysaccharide) or suppression (negative score, related to blank control) of cell proliferation. The test substance was evaluated under these conditions at 10, 1, 0.1, 0.01 and 0.001 uM. After overnight incubation, 2 uCi [$^3$H] thymidine incorporation was assessed by liquid scintillation counting.

B-lymphocyte Proliferation+LPS

Procedure: B-cells were isolated from mouse spleen using conventional procedures, and suspended in DMEM. $10^6$ cells/ml were incubated overnight at 37° C. in the presence of 10 ug/ml lipopolysaccharide (LPS) to assess stimulation (positive score, related to 1 ng/ml rat interleukin-5) or suppression (negative score, related to control) of cell proliferation. The test substance was evaluated under these conditions at 10, 1, 0.1, and 0.01 uM. After overnight incubation, 2 uCi [$^3$H] thymidine was added to each well. Cells were harvested after an additional 48 hour incubation, and thymidine incorporation assessed by liquid scintillation counting.

T-lymphocyte Proliferation

Procedure: T-cells were isolated from mouse thymus using conventional procedures, and suspended in DMEM. $5 \times 10^6$ cells/ml were incubated overnight at 37° C. to assess stimulation (positive score, related to 3 ug/ml Concanavalin A) or suppression (negative score, related to blank control) of cell proliferation. Test substance was evaluated under these conditions at 10, 1, 0.1, 0.01, 0.001 uM. After overnight incubation, 2 uCi [$^3$H] thymidine was added to each well. Cells were harvested after an additional 48 hour incubation, and thymidine incorporation assessed by liquid scintillation counting.

T-lymphocyte Proliferation+Con A

Procedure: T-cells were isolated from mouse thymus using conventional procedures, and suspended in DMEM. $5 \times 10^6$ cells/ml are incubated overnight at 37° C. in the presence of 3 ug/ml Con A to assess stimulation (positive score, related to 10 U/ml rat interleukin-2) or suppression (negative score, related to control) of cell proliferation. Test substance was evaluated under these conditions at 10, 1, 0.1 and 0.01 uM. After overnight incubation, 2 uCi [$^3$H] thymidine is added to each well. Cells were harvested after an additional 48 hour incubation, and thymidine incorporation assessed by liquid scintillation counting.

TABLE 5

ASSAY SOLV: 0.5% DMSO

| FUNCTIONAL ASSAYS | SOURCE | % Stimulation (+)/Suppression (−) (μM) | | | | |
| --- | --- | --- | --- | --- | --- | --- |
| | | 10 | 1 | 0.1 | 0.01 | 0.001 |
| B-Cell Proliferation | Mouse Spleen | 2 | 9 | 10 | 8 | 4 |
| B-Cell Proliferation + LPS | Mouse Spleen | −54 | −25 | −9 | −15 | 13 |

TABLE 5-continued

ASSAY   SOLV: 0.5% DMSO

| FUNCTIONAL ASSAYS | SOURCE | % Stimulation (+)/Suppression (−) (µM) | | | | |
|---|---|---|---|---|---|---|
| | | 10 | 1 | 0.1 | 0.01 | 0.001 |
| T - Cell Proliferation | Mouse Thymus | −24 | −3 | 1 | 0 | −2 |
| T - Cell Proliferation + ConA | Mouse Thymus | −43 | 3 | 7 | 7 | 4 |

IN VIVO TESTS

Immunopharmacological tests
Immunostimulation (Cellular)-Oxazolone-Induced Delayed Type Hypersensitivity The test substance was administered i.p to groups of 5 mice, 1 hour before application (sensitization) of oxazolone (0.1 ml of 5% solution) to the pre-shaven abdominal surface. Seven days later, 25 µl of a 2% solution of oxazolone was applied (challenge) to the right ear, with vehicle being applied to the left ear. After 24 hours, each mouse was sacrificed and ear thickness measured with a Dyer Model micrometer gauge. Greater than 30 percent enhancement is considered immunostimulant activity.

The shaved abdominal surface of groups of 5 mice were sensitized by application of 0.1 ml of 5% oxazolone. The test substance was administered i.p after 1 hour and then daily for 5 consecutive doses. After an additional 4 days, the animals were challenged by application of 25 ul of 5% oxazolone to the right ear. Twenty-four hours later, ear thickness was measured with a Dyer Model micrometer gauge.

A 50 percent or greater decrease in drug-treated versus control animals is considered significant immunosuppressant activity.

| Immunostimulation (Cellular): Oxazolone-Induced Delayed Type Hypersensitivity | | | | | | |
|---|---|---|---|---|---|---|
| | | | EAR THICKNESS MEASUREMENT (X̄ ± SEM) × 0.01 mm | | | |
| COMPOUND | ROUTE | DOSE (mg/kg) | Left Ear (No Oxa.) | Right Ear (24 hrs Oxa.) | Swelling (R − L) | Inc. % |
| Vehicle Control (PBS) | IP | 20 ml/kg × 5 | 23.6 ± 0.7 | 41.0 ± 3.0 | 17.4 ± 2.8 | |
| rhamnolipid | IP | 100 × 5 | 21.3 ± 1.0 | 32.3 ± 2.0 | 11.0 ± 1.1 | −37** |
| rhamnolipid | IP | 10 × 5 | 20.2 ± 0.4 | 40.0 ± 1.6 | 19.8 ± 1.9 | 14 |
| rhamnolipid | IP | 1 × 5 | 20.6 ± 0.9 | 39.6 ± 2.2 | 19.0 ± 2.2 | 9 |
| rhamnolipid | IP | 0.1 × 5 | 19.4 ± 1.1 | 34.8 ± 1.8 | 15.4 ± 1.7 | −11 |
| Azimexone | IP | 100 × 5 | 21.4 ± 0.5 | 44.2 ± 0.7 | 22.8 ± 0.9 | 31 |

Note:
**means that 1/5 died on Day 2

Immunosuppression (Cellular)-Oxazolone-Induced Delayed Type Hypersensitivity

| Immunosupression (Cellular): Oxazolone-Induced Delayed Type Hypersensitivity | | | | | | |
|---|---|---|---|---|---|---|
| Mice: ICR (female), 25 ± 2 gms n = 5/group | | | | | | |
| | | | | EAR THICKNESS MEASUREMENT (X̄ ± SEM) × 0.01 mm | | |
| COMPOUND | ROUTE | DOSE (mg/kg) | Left Ear (No oxa.) | Right Ear (24 hrs Oxa.) | Swelling (R − L) | Inh. % |
| Vehicle Control (PBS) | IP | 20 ml/kg × 5 | 21.6 ± 0.7 | 47.4 ± 1.7 | 25.8 ± 1.7 | |
| rhamnolipid | IP | 100 × 5 | 19.0 ± 0.9 | 382 ± 1.3 | 19.2 ± 0.6 | 26 |
| rhamnolipid | IP | 10 × 5 | 20.8 ± 0.7 | 41.6 ± 1.2 | 20.8 ± 1.2 | 19 |
| rhamnolipid | IP | 1 × 5 | 21.0 ± 0.5 | 41.2 ± 1.8 | 20.2 ± 1.7 | 22 |
| rhamnolipid | IP | 0.1 × 5 | 21.0 ± 0.8 | 40.6 ± 3.0 | 19.6 ± 2.9 | 16 |
| Cyclophosphamide | IP | 30 × 5 | 19.0 ± 0.4 | 29.6 ± 2.2 | 10.6 ± 1.8 | 59 |

Immunosuppression (Cellular): Oxazolone-Induced Delayed Type Hypersensitivity
Immunostimulation and Immunosuppression (Humoral)—Sheep Red Blood Cell (SRBC) Hemagglutination Groups of 6 mice were sensitized by the IV injection of 0.2 ml of a 2% SRBC suspension. On the $9^{th}$ day following sensitization, blood samples were withdrawn from the orbital sinus and equal parts of complement inactivated serum from the group of 6 mice were pooled to yield a single 0.25 ml sample. Serial 2-fold dilutions were then carried out 10 times in the presence of added complement. Serum titer was expressed as the reciprocal of the dilution exhibiting complete hemolysis. Serum titers of less than 16 or greater than 128 are considered significant and indicate possible immunosuppressant and immunostimulant activity, respectively.

For immunostimulant activity, test substance or vehicle was administered i.p. to groups of mice for 3 consecutive days, and sensitized to SRBCs 2 hours after the third (last) injection. For immunosuppressant activity, test substance or vehicle was administered i.p. to groups of mice for 3 consecutive days beginning 2 hours after sensitization to SRBCs.

| COMPOUND | ROUTE | DOSE (mg/kg) | SERUM TITER (Reciprocal Serum Dilution) | NOTE |
|---|---|---|---|---|
| Immunostimulation (Humoral): Sheep Red Blood Cell (SRBC) Hemagglutination | | | | |
| Vehicle Control (PBS) | IP | 20 ml/kg × 3 | 32 | |
| rhamnolipid | IP | 100 × 3 | 8 | 1/6 died on Day 3 |
| rhamnolipid | IP | 10 × 3 | 128 | |
| rhamnolipid | IP | 1 × 3 | 64 | |
| rhamnolipid | IP | 0.1 × 3 | 64 | |
| Levamisole | IP | 30 × 3 | 128 | |
| Immunosupression (Humoral): Sheep Red Blood Cell (SRBC) Hemagglutination Mice: ICR (female), 25 ± 2 gms n = 6/group | | | | |
| Vehicle Control (PBS) | IP | 20 ml/kg × 3 | 32 | |
| rhamnolipid | IP | 100 × 3 | 16 | 2/6 died on Day 3 |
| rhamnolipid | IP | 10 × 3 | 128 | |
| rhamnolipid | IP | 1 × 3 | 32 | |
| rhamnolipid | IP | 0.1 × 3 | 32 | |
| Cyclo-phosphamide | IP | 30 × 3 | 4 | |

Immunorestoration

Immunosuppression with Cyclophosphamide and Infection with *Candida albicans*

The test substance or vehicle was administered i.p. to groups of 10 mice on days 1, 3, and 5, with cyclophosphamide (25 mg/kg p.o.) administered on days 2, 4, and 6. One day after the last immunosuppressant dose, the mice were challenged with a suspension of *C. albicans* sufficient to result in 90 to 100 percent mortality within 10 days in the vehicle treated control group. A greater than 30 percent survival for any drug treated group is considered significant, and possibly a result of immunorestorant activity.

| | | | Immunorestoration: Immunosuppression With Cyclophosphamide and Infection With *Candida albicans* Mice: ICR (female), 25 ± 2 gms n = 10/group | | | | | |
|---|---|---|---|---|---|---|---|---|
| | | | Days Post-Inoculum *C. albicans* (Death #/10 Mice) | | | | Response | |
| Compound | Route | Dose (mg/kg) | 0–1 | 2–3 | 4–6 | 7–9 | Survivor No. | Inc. % |
| Vehicle Control (PBS) | IP | 20 ml/kg × 3 | 0 | 0 | 1 | 0 | 9 | |
| Cyclophosphamide | PO | 30 × 3 | 3 | 2 | 2 | 1 | 2 | |
| Rhamnolipid + Cyclophosphamide | IP | 100 × 3 | 1 | 1 | 1 | 0 | 7 | 50 |
| Rhamnolipid + Cyclophosphamide | IP | 10 × 3 | 2 | 1 | 1 | 0 | 6 | 40 |
| Rhamnolipid + Cyclophosphamide | IP | 1 × 3 | 2 | 2 | 1 | 1 | 4 | 20 |
| Rhamnolipid + Cyclophosphamide | IP | 0.1 × 3 | 2 | 1 | 1 | 2 | 4 | 20 |
| Azimexone + Cyclophosphamide | IP | 100 × 3 | 2 | 1 | 1 | 1 | 5 | 30 |

Immunomodulation
Infection with Candida albicans

The test compound or vehicle was administered i.p. to groups of 10 mice 1 hour before IV, challenge with suspension of C. albicans sufficient to result in 90 to 100% mortality within 10 days in the vehicle treated control group. A greater than 30 percent survival for any treated group is considered very significant, and possibly a result of immunomodulation, while an increase of 20% is considered a moderate immunomodulation activity.

Immunomodulation: Infection with Candida albicans
Mice: ICR (female), 25 ± 2 gms
n = 10/group

| Compound | Route | Dose (mg/kg) | Days Post-Inoculum C. albicans (Death #/10 mice) | | | | Response | |
|---|---|---|---|---|---|---|---|---|
| | | | 0–1 | 2–3 | 4–6 | 7–9 | Survivor No. | Inc. % |
| Vehicle Control (PBS) | IP | 20 ml/kg × 3 | 2 | 6 | 0 | 0 | 2 | |
| Rhamnolipid | IP | 100 × 3 | 6 | 4 | 0 | 0 | 0 | 0 |
| Rhamnolipid | IP | 10 × 3 | 0 | 5 | 1 | 0 | 4 | 20 |
| Rhamnolipid | IP | 1 × 3 | 2 | 3 | 1 | 0 | 4 | 20 |
| Rhamnolipid | IP | 0.1 × 3 | 3 | 4 | 1 | 0 | 2 | 0 |
| Levamisole | IP | 30 | 3 | 3 | 0 | 0 | 4 | 20 |

Activity of di-rhamnolipid on blood count in mouse
Blood count after application of di-rhamnolipid

| | Control | Rhamnolipid |
|---|---|---|
| 4th day after Application | | |
| Leukocytes | $(17.12 \pm 1.70) \times 10^3$ | $(17.42 \pm 3.18) \times 10^3$ |
| Erythrocytes | $(7.44 \pm 0.50) \times 10^6$ | $(7.82 \pm 0.96) \times 10^6$ |
| Neutrophils | 28.20 ± 3.03 | 42.80 ± 11.12 |
| Basophiles | 0.40 ± 0.89 | 0.75 ± 0.15 |
| Eosinophiles | 0 | 0.60 ± 1.34 |
| Monocytes | 1.00 ± 1.73 | 2.60 ± 1.94 |
| Lymphocyts | 70.40 ± 4.15 | 53.40 ± 11.14 |
| nRBC | 0 | 0 |
| 29th day after application | | |
| Leukocytes | $(18.56 \pm 2.03) \times 10^3$ | $(19.50 \pm 1.14) \times 10^3$ |
| Erythrocytes | $(7.23 \pm 0.93) \times 10^6$ | $(7.13 \pm 0.89) \times 10^6$ |
| Neutrophils | 28.20 ± 3.03 | 40.50 ± 9.19 |
| Basophiles | 0.40 ± 0.89 | 0.50 ± 0.70 |
| Eosinophiles | 0 | 0.50 ± 0.70 |
| Monocytes | 1.00 ± 1.73 | 2.00 ± 2.80 |
| Lymphocytes | 70.40 ± 4.15 | 56.50 ± 12.02 |
| nRBC | 0 | 0 |

CONCLUSION: Rhamnolipid (4th day and up to 29th day after application) significantly increased neuthrophils and decreased lymphocytes.

Structural chromosomal aberrations analysis (in vivo test)

Results of analysis on the chromosomal structural aberrations in the rat bone marrow cells showed that a concentration of rhamnolipid (II) of 31.5 mg/kg of the animal body weight does not cause chromosomal damages. In the control and treated samples there were individual breaks of chromosomes and chromatides accompanied with acentric fragments in only 1% of the analyzed cells. Such results are not statistically significant and are accepted as a technical error and not as an interaction of rhamnolipid (II) with the bone marrow DNA.

General toxicological research

The objectives of this study were to determine $LD_{90}$, $LD_{50}$, $LD_{10}$, and target organ toxicity in mice, resulting from a single intravenous dose, five intraperitoneal doses during five days (one per day) and five intraperitoneal doses in one day; to provide an estimate of drug toxicity; and to obtain data from a rodent species to be able to determine the initial dose for carcinogenesis studies in rodents.

Tests were performed on mice C57B1/6, Animal source: Bantin and Kingman. This was done following the procedures described elsewhere in Technical Report Series, National Toxicology Program, U.S. Department of Health and Human services.

Range-finding study phase (single dose)

The lower bracket dose (LBD) was 67.5 mg/kg. The upper bracket dose (UBD) was 127.5 mg/kg.

After IV administration of the tested rhamnolipid, it was also shown that the average $LD_{50}$ for a mouse was 105.0 mg/kg.

In the Range-finding study phase (single dose), single dose toxicity was 7.5 mg/kg after IV application of rhamnolipid II. The fourth day after application of rhamnolipid (II), a significant increase of neutrophils and a significant decrease of lymphocytes was observed. During the observation period there were no changes in behavior and appearance of the treated mice.

Range-finding study phase (five doses per five days, one dose per day)

The lower bracket dose (LBD) was 45 mg/kg. The upper bracket dose (UBD) was 125 mg/kg.

In the Range-finding study phase (five doses per five days, one dose per day), the single dose toxicity was 5 mg/kg after intraperitoneal application of rhamnolipid II. The fourth day after application of rhamnolipid II, a significant increase of neutrophils, basophiles, eosinophiles and a significant decrease of lymphocytes was observed. During the observation period, there were no changes in behavior and appearance of the treated mice.

Range-finding study phase (five doses per day)

The lower bracket dose (LBD) was 45 mg/kg. The upper bracket dose (UBD) was 125 mg/kg.

In the Range-finding study phase (five doses per day), the five dose toxicity was 5 mg/kg after intraperitoneal application of rhamnolipid II. The fourth day after application of rhamnolipid (II), there were no statistical differences between rhamnolipid (II) and control.

Histopathologic examinations

Examinations were made in all tests on the following tissues from each mouse necropsied: bone (femur), bone marrow (femur)-slide only, brain, colon, duodenum, testes, heart, kidneys, liver, lungs (infuse with formalin), pancreas, spleen, muscle, adrenal nodes, uterus, gastric.

Conclusion

In conclusion, complete pathohistological examination report, on all organs in all control and experimental animals, shows that in the experimental group none of the regressive-progressive or inflammatory type of changes were detected, for the appearance of which the experimental substance could be responsible.

Clinical Results in Treatment of Psoriasis 17 patients, 11 men and 6 women, were treated with rhamnolipid (II). Among these, 12 patients were suffering from Psoriasis, 2 from Neurodermitis, 1 from Lichen ruber planus, 1 from Serborhoic dermatitis and one from Dermatitis circumscripta unilocularis eczematoides.

The age of patients ranged from 19 to 80 years old.

Psoriatic patients have previously been treated several times and have suffered from this disease for 1.5 to 25 years.

The experimental treatment of the first 6 psoriatic patients started during May and June of 1991.

All patients were treated by application of a cream containing rhamnolipid II over selected psoriatic localities, 2 times a day for 21 days.

The remaining psoriatic localities on the body were treated with local corticosteroid.

The treatment and the follow-up of the patients was a "double blind" experiment.

The therapeutic efficacy was monitored by PASI-index.

After observing positive results with the first six psoriatic patients, who were treated and monitored until the end of the year, rhamnolipid was applied on larger psoriatic surfaces (up to a half of the patient's body where psoriatic lesions existed). Also, occlusions were used (up to 48 hours) and the duration and usage of occlusions was prolonged up to 35 days.

With such an approach, better results were observed by the time the patients left the hospital and relapses were less frequent. With some patients no relapses were observed even after 10 months following the treatment.

Blood samples for lab tests were taken from all twelve patients on the first and last day of treatment. Although numerous lab tests were performed, no altered results of the tests were observed, as a consequence of local treatment of psoriatic lesions with the present rhamnolipid II.

Patients were seen 3, 6 and 9 months after treatment and they were instructed not to apply any other local preparations at the same localities where rhamnolipic II was applied.

The conclusion after the follow up was that good results were obtained on all psoriatic lesions where rhamnolipid II was applied. The substance a curvature effect, in most cases, sooner or in the same period of time it took local corticosteroid to activate. The appearance of relapses was significantly delayed even 10 months after the treatment with rhamnolipid II, as opposed to patients treated with local corticosteroid who are still in remission.

The appearance of relapses is believed to be linked to the duration of rhamnolipid II treatment at psoriatic localities.

Two patients with Neurodermitis were treated at the beginning of 1992. Rhamnolipid II was applied on affected regions twice a day; occlusions were applied as well (up to 24 hours).

The treatment and monitoring of patients was, again, a "double blind" experiment. Other affected regions where corticosteroids were applied were used for comparison.

Improvements were observed rapidly, faster than in cases when corticosteroids were applied with relapses occurring a bit later as compared to the regions where local corticosteroids were applied.

One patient suffering from each of these illnesses seborhoic dermatitis, Lichen ruber planus, Dermatitis circumscripta unilocularis, was completely cured.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A pharmaceutical composition for treating an autoimmune diseases, comprising: as active ingredient, one or more rhamnolipids of formula (I):

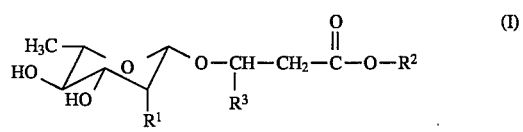

wherein $R^1$ is H or α-L-rhamnopyranosyl;

$R^2$ is H or $—CH(R^4)—CH_2—COOH$;

$R^3$ is $(C_5–C_{20})$-saturated, mono or polyunsaturated hydrocarbyl and $R^4$ is $(C_5–C_{20})$-saturated, mono or polyunsaturated hydrocarbyl, or a pharmaceutically acceptable salt thereof;

in a pharmaceutically acceptable carrier.

2. The pharmaceutical composition of claim 1, wherein said pharmaceutical composition is in a form selected from the group consisting of creams, lotions, injectable solutions, tablets, capsules and orally consumable solutions and suspensions.

3. The pharmaceutical composition of claim 1, wherein said rhamnolipid is a rhamnolipid of formula (II):

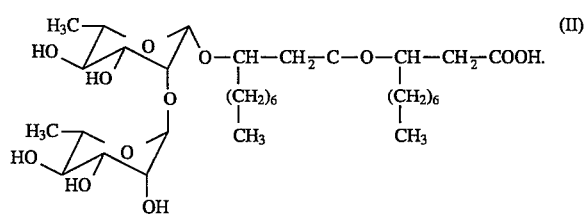

4. The pharmaceutical composition of claim 1, wherein said one or more rhamnolipids of formula (I) have $R^1$=α-L-rhamnopyranosyl.

5. The pharmaceutical composition of claim 1, wherein said one or more rhamnolipids of formula (I) have $R^3$=—$(CH_2)_x$—$CH_3$, wherein x is from 4 to 20.

6. The pharmaceutical composition of claim 1, wherein said one or more rhamnolipids of formula (I) have $R^4$=—$(CH_2)_x$—$CH_3$, wherein x is from 4 to 20.

* * * * *

UNITED STATES PATENT AND TRADEMARK OFFICE
CERTIFICATE OF CORRECTION

PATENT NO. : 5,514,661
DATED : May 7, 1996
INVENTOR(S) : Goran PILJAC, et al.

It is certified that error appears in the above-indentified patent and that said Letters Patent is hereby corrected as shown below:

On the title page, Item [60], the Related U.S. Application Data, should read:

--[60] Division of Ser. No. 277,975, July 20, 1994, Pat. No. 5,466,675, which is a continuation-in-part of Ser. No. 866,691, Apr. 10, 1992, abandoned.--

Signed and Sealed this

Thirteenth Day of August, 1996

*Attest:*

BRUCE LEHMAN

*Attesting Officer*    Commissioner of Patents and Trademarks